(12) United States Patent  (10) Patent No.: US 8,449,493 B2
Babaev  (45) Date of Patent: May 28, 2013

(54) ULTRASONIC SYRINGE METHOD

(76) Inventor: Eilaz Babaev, Minnetonka, MN (US)

( * ) Notice: Subject to any disclaimer, the term of this patent is extended or adjusted under 35 U.S.C. 154(b) by 1244 days.

(21) Appl. No.: 12/017,072

(22) Filed: Jan. 21, 2008

(65) Prior Publication Data

US 2009/0187136 A1 Jul. 23, 2009

(51) Int. Cl.
A61B 17/20 (2006.01)

(52) U.S. Cl.
USPC .......................................................... 604/22

(58) Field of Classification Search
USPC ...... 604/19, 22, 181, 187, 500, 501; 600/459, 600/437, 461
See application file for complete search history.

(56) References Cited

U.S. PATENT DOCUMENTS

| | | |
|---|---|---|
| 530,187 A | 12/1894 | Laskey |
| 786,697 A | 4/1905 | Wackenhuth |
| 900,565 A | 10/1908 | Mayers et al. |
| 1,704,678 A | 3/1929 | Brown |
| 1,771,219 A | 7/1930 | Heln |
| 2,717,598 A | 9/1955 | Krasno |
| 2,773,500 A | 12/1956 | Young |
| 2,911,972 A | 11/1959 | Ellnger |
| 2,935,067 A | 5/1960 | Bouet |
| 2,966,175 A | 12/1960 | Hyde |
| 3,605,745 A | 9/1971 | Hodosh |
| 3,935,883 A | 2/1976 | Stach et al. |
| 3,989,045 A | 11/1976 | Van Eck |
| 3,991,757 A | 11/1976 | van Leer |
| 3,998,223 A | 12/1976 | Dawe |
| 4,007,739 A | 2/1977 | Bron et al. |
| 4,030,498 A | 6/1977 | Tompkins |
| 4,031,889 A | 6/1977 | Pike |
| 4,155,490 A | 5/1979 | Glenn |
| 4,323,066 A | 4/1982 | Bourdon |
| 4,484,915 A | 11/1984 | Tartaglia |
| 4,492,317 A | 1/1985 | Guess et al. |
| 4,515,591 A | 5/1985 | Hemmerich et al. |
| 4,596,556 A | 6/1986 | Morrow et al. |
| 4,617,016 A | 10/1986 | Blomberg |
| 4,854,324 A | 8/1989 | Hirschman et al. |
| 5,176,642 A | 1/1993 | Clement |
| 5,269,762 A | 12/1993 | Armbruster et al. |
| 5,311,871 A | 5/1994 | Yock |
| 5,368,568 A | 11/1994 | Pitts et al. |
| 5,437,606 A | 8/1995 | Tsukamoto |
| 5,512,048 A | 4/1996 | Slettenmark |
| 5,584,814 A | 12/1996 | Schuster et al. |

(Continued)

FOREIGN PATENT DOCUMENTS

WO  WO 97/17933  5/1987

Primary Examiner — Kevin C Sirmons
Assistant Examiner — Imani Hayman

(57) ABSTRACT

The present invention relates to an ultrasonic syringe and method of use for delivery and withdrawal of fluids from a human and/or animal patient. The ultrasonic syringe apparatus comprises a generator, a movable ultrasound transducer, a barrel, an ultrasound transducer tip, a radiation surface, an orifice located at the front end of the barrel, and a syringe head. The apparatus may further comprise a channel, a valve located on the distal end of the channel, and an orifice within the side wall which enables fluids to be delivered into the barrel. Ultrasonic waves emitting from the radiation surface induce vibrations within the fluids, sonicating the fluids, thereby eliminating the pain and discomfort associated with receiving injections, reducing and/or eliminating the force required to administer the injection, decreasing delivery time of the fluids into the body, and delivering ultrasonic energy to the tissue via the sonicated fluids.

19 Claims, 3 Drawing Sheets

U.S. PATENT DOCUMENTS

| | | | |
|---|---|---|---|
| 5,690,618 A | 11/1997 | Smith et al. | |
| 5,803,106 A | 9/1998 | Cohen et al. | |
| 5,830,194 A | 11/1998 | Anwar et al. | |
| 5,882,338 A | 3/1999 | Gray | |
| 5,902,270 A | 5/1999 | Jentzen | |
| 6,030,368 A | 2/2000 | Anwar et al. | |
| 6,048,334 A | 4/2000 | Hirschman et al. | |
| 6,053,424 A | 4/2000 | Gipson et al. | |
| 6,053,894 A | 4/2000 | Shadd, Jr. | |
| 6,083,200 A | 7/2000 | Grimm et al. | |
| 6,379,328 B1 | 4/2002 | Mac Clay | |
| 6,380,264 B1 | 4/2002 | Jameson et al. | |
| 6,436,075 B1 | 8/2002 | Liao | |
| 6,527,751 B2 | 3/2003 | Fischer et al. | |
| 6,582,399 B1 | 6/2003 | Smith et al. | |
| 6,585,700 B1 | 7/2003 | Trocki et al. | |
| 6,623,444 B2 | 9/2003 | Babaev | |
| 6,723,064 B2 | 4/2004 | Babaev | |
| 6,776,352 B2 * | 8/2004 | Jameson | 239/1 |
| 6,923,790 B2 | 8/2005 | Lal et al. | |
| 7,118,852 B2 * | 10/2006 | Purdum | 435/2 |
| 2004/0266890 A1 * | 12/2004 | Kipp et al. | 516/20 |
| 2007/0140041 A1 * | 6/2007 | Sparey-Taylor et al. | 366/127 |
| 2008/0063604 A1 * | 3/2008 | Claudio | 424/9.52 |

* cited by examiner

ULTRASONIC SYRINGE METHOD

BACKGROUND OF THE INVENTION

The present invention relates to a medical apparatus method for the delivery or withdrawal of fluids from a patient, and more particularly, to an ultrasonic syringe.

Various infections, conditions, and diseases of the body can be difficult to treat with out the administering of medications via transdermal injections. Different types of fluids, such as, but not limited to, medications, vaccines, water, saline solutions, and blood products can be injected into the body or withdrawn from the body. In medical practice, such fluids are administered in several ways, such as, but not limited to subcutaneously, intravenously, and/or intramuscularly depending on an identified treatment purpose. Also, injections are the best way to deliver a precise dose of medication quickly. When given, fluids such as drugs are immediately delivered to the blood stream, and tend to take effect more quickly than when given by any other route.

The fluids are typically administered to the patient or withdrawn from the patient by a practitioner, who may be a physician, nurse, orderly, nurse practitioner, or other such individual.

A typical manual syringe is a device for introducing and/or injecting fluids into or withdrawing them from the body. Generally, a syringe consists of a hypodermic needle attached to a hollow cylinder that is fitted with a sliding plunger. Fluid is expelled from the syringe when the plunger is depressed. Physical force is needed to push in the plunger in order to discharge fluid into the patient's body. The practitioner administering the injection is required to use physical force to discharge the fluid from the syringe into the body. Such use of physical force can cause injury not only to the patient but also to the practitioner administering the injections.

The physical force required to administer the injection causes tension and/or pain on the practitioner's arms, shoulders, fingers and/or thumb, especially since several injections are administered to different patients each day. Furthermore, it is very painful for the patient when the hypodermic needle is inserted into the body with such physical force. The patient is typically already in pain and receiving the injection should not increase the pain.

These manual syringe devices provide uneven thumb and/or finger pressure when injection is being, delivered, the practitioner has very little control over the flow rate of the fluid exiting the hypodermic needle, there is also very poor control of hypodermic needle tip which can lead to damage to skin, tissue and/or veins, and generally unnecessary pain and discomfort in patient.

Various powered and/or electrical syringes are also present in the prior art. These devices were developed to overcome the problems associated with manual syringes, however, these electronically and/or mechanically powered syringes are not without problems. These devices do not reduce and/or eliminate the pain and discomfort associated with receiving injections, sonicate fluids prior to and during delivery into the body, and are sometimes cumbersome to use.

Current syringes fail to eliminate the pain and/or discomfort associated with administering an injection to the body of a patient. Additionally, such syringes fail to decrease drug delivery time and force required in administering the injection. Hence, there is a need for a syringe with faster administration time, eliminating the pressure on the practitioner's arms, shoulders, fingers and/or thumb, especially since several injections are administered to different patients each day, therefore increasing the quality of work life for the practitioner, and reducing the time spent delivering drugs via injections to the body.

SUMMARY OF THE INVENTION

Apparatus and methods in accordance with the present inventions may resolve many of the needs and shortcomings discussed above and will provide additional improvements and advantages as will be recognized by those skilled in the art upon review of the present disclosure.

The present inventions provide an ultrasonic syringe for delivering and withdrawing fluids from the body. The ultrasonic syringe apparatus comprises an ultrasound generator, a movable ultrasound transducer, a transducer tip at the distal end of the ultrasound transducer, a radiation surface at distal end of transducer tip, a barrel, and a syringe head.

The apparatus of the present invention may further comprise an attachment stub configured into the barrel. The attachment stub may include a valve for the regulation of the flow of fluid into the barrel. Ultrasonic waves emitting through the transducer tip at the radiation surface may sonicate fluid contained within the cavity defined by the barrel and the transducer tip by inducing vibrations within these fluids. The sonicated fluids may then be injected into the body through a hypodermic needle that may be attached to the syringe head. This use in sonodynamic therapy provides for the activation of therapeutic agents by the ultrasound essentially at the same time it is being administered to the body.

Sonicating fluids prior and during delivery to the body provides several advantages to the patient, such as, but not limited to, elimination and/or reduction of pain and discomfort from receiving the injection, elimination of tissue damage during injection, and reduction of infection in the patient as a result of the anesthetic and antimicrobial properties of ultrasound.

The ultrasonic syringe may enable the practitioner administering the injection to do so without applying physical force, therefore, physical force may be decreased and/or eliminated. The ultrasonic waves emitted from the radiation surface within the barrel may push the fluids through the hypodermic needle into the body.

Injecting fluids subcutaneously, intravenously, intramuscularly, and/or through catheters into the body with the present invention may entail filling the cavity portion of the ultrasonic syringe barrel with the selected fluids, activating the transducer and depressing the ultrasound transducer. The ultrasound transducer may be depressed manually or mechanically. When depressed manually, minimal force may be required to push the transducer down because the ultrasonic waves emitting from the radiation surface reduces the physical force required by the practitioner to depress the transducer. The ultrasound waves emitting through the radiation surface at the distal end of the ultrasound tip induce vibrations within the barrel causing the fluids to be sonicated. The pumping action provided by the ultrasound energy emitted from the ultrasound transducer may also be controlled by adjusting the amplitude of the ultrasonic vibrations. Sonicated fluids may move through the orifice located at the front end of the barrel to the syringe head, and may be injected into the patient's body.

The ultrasonic syringe also has the ability of enhancing therapeutic effects and reducing the force required for injection by changing the viscosity of the fluid being injected through the action of the ultrasound energy on the fluid physical properties.

The present invention may be used to introduce and/or deliver fluids into the body. Activating the ultrasound transducer creates vibrations within the transducer tip resulting in the emission of ultrasonic waves from the radiation surface. The ultrasonic waves induce vibrations within the fluids in the barrel. Ultrasonic waves coming in contact with the fluids sonicate and activate the fluids as they are delivered into the body.

The barrel of the present invention holds the fluid before it may be injected into the body of a patient. The width of the barrel may be variable and depends on the use; such as use on a human body, or use on an animal, and/or on the amount of fluids needed. The barrel may be fabricated from a disposable and/or autoclavable plastic material, polymer, metal, glass, and/or any combination thereof. Material selection may be based on the desired effect of the barrel on the emitted ultrasound waves. Depending on the particular application, it may be desirable for the barrel to reflect ultrasound waves, adsorb ultrasound waves or transmit ultrasound waves and materials of construction would be selected accordingly. The barrel may be formed in a variety of shapes such as, but not limited to cylindrical, oval and/or rectangular. The back end may be the area opposite and away from the syringe head. The front end of the barrel may be located at the proximal end of the syringe head. An orifice located at the front end of the barrel serves to transport the fluids out of the barrel. An orifice located at the back end of the barrel receives the transducer tip within the barrel.

The ultrasound transducer of the present invention may be located at the back end of the barrel. The ultrasound transducer may be imbedded into the barrel and/or detachable from the barrel. An ultrasound generator may be connected to the ultrasound transducer. The ultrasound generator and transducer may be a single piece imbedded into each other. Alternatively, the ultrasound transducer may be battery operated. The ultrasound transducer may be a movable part that slides forward and backwards within the barrel. Sliding forward, the ultrasound transducer pushes the fluids in the barrel towards an orifice located at the front end of the barrel. Emitted ultrasonic energy eases the push of the fluids, consequently, the fluids in the barrel exit the orifice moving through the hypodermic needle into the patient's body.

The present invention may also be used to withdraw fluids, such as, but not limited to blood samples, from the body of a human and/or animal patient. After the hypodermic needle may be introduced into the body from which the fluid sample may be to be withdrawn, the ultrasound transducer may be activated creating a vacuum within the barrel. The ultrasound transducer may be pulled back away from the front end of the barrel manually and/or by mechanical means. As the transducer may be pulled back away from the front end of the barrel towards the back end, ultrasonic waves induce vibrations within the drawn fluids in the barrel.

Alternatively, fluids may be introduced into the barrel through one or multiple orifices within the side wall of the barrel. In an alternative embodiment, the present invention may comprise an orifice located within the side wall of the barrel, and a valve. The orifice may further comprise a channel originating from the orifice located within the side wall of the barrel and terminating at a valve. The valve may be located at the distal end of the channel. Fluids may be delivered to the barrel through the valve. The valve further prevents fluids from flowing back out from the orifice within the side wall of the barrel into the channel. The valve may be manually and/or mechanically controlled.

At least one of the materials may, but need not, be a carrier for at least one of the other materials utilized. Acceptable carriers may include, but are not limited to, water, a saline solution, and/or alcohol. At least one of the materials may, but need not, be a pharmaceutical or therapeutic agent. Preferably, at least one of the materials is preferably capable of eliciting a positive therapeutic effect, such as, but not limited to oxygen.

The vibrations induced by the ultrasound energy in the barrel, and the sonicated fluids reduce patient pain during the administration of the injection. Penetration force may be also decreased. The ultrasonic waves reduce the physical force required to administer the injection, hence, reducing the tension and/or eliminating the pain in the practitioners arms, shoulders, fingers and/or thumb. Ultrasonic waves may be also delivered to the tissue via sonicated fluids providing therapeutic benefits to the patient.

Other features and advantages of the invention will become apparent from the following detailed description, and from the claims.

DETAILED DESCRIPTION OF THE INVENTION

Figure 1:
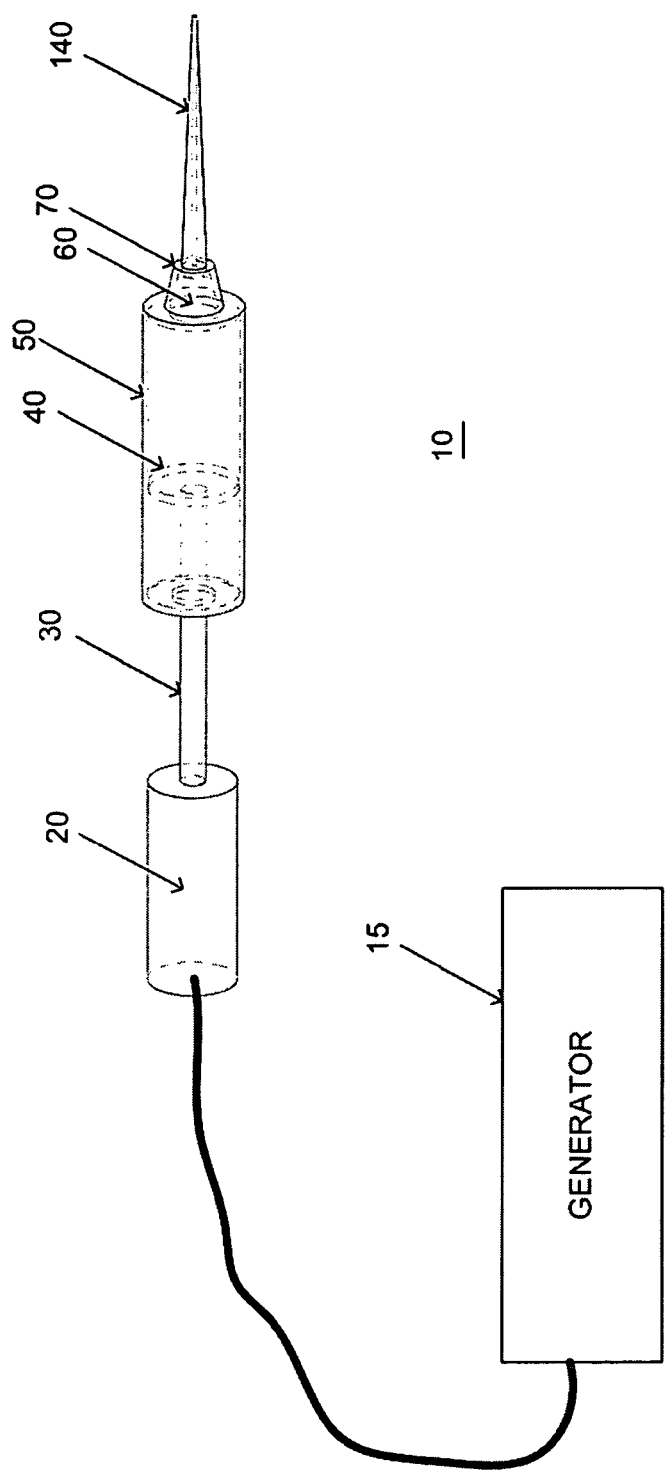
FIG. 1 illustrates a dimensional schematic view of aspects of an exemplary embodiment of an ultrasonic syringe according to the present inventions.

The figures generally illustrate embodiments of an ultrasonic syringe 10 including aspects of the present inventions. The particular exemplary embodiments of the ultrasonic syringe 10 illustrated in the figures have been chosen for ease of explanation and understanding of various aspects of the present inventions. These illustrated embodiments are not meant to limit the scope of coverage but instead to assist in understanding the context of the language used in this specification and the appended claims. Accordingly, many variations from the illustrated embodiments may be encompassed by the appended claims.

The present inventions provide an ultrasonic syringe 10 for the delivery of fluids 25 to a patient or the withdrawal of fluids 25 from a patient. The ultrasonic syringe 10 according to the present invention may provide increased comfort to the patient as well as to the practitioner administering the fluid 25. The effectiveness of the delivery of the fluid 25 may also be increased by the ultrasonic syringe 10 according to the present inventions.

As generally illustrated throughout the Figures, the ultrasonic syringe 10 generally includes an ultrasound generator 15 connected to a movable ultrasound transducer 20. A transducer tip 30 may be located at the distal end of the ultrasound transducer 20. The distal end of the transducer tip 30 may be configured as a radiation surface 40. At least portions of the transducer tip may be slideably received inside a barrel 50. An orifice 60 located at the front end of barrel 50 defines a passage 56 to syringe head 70. Hypodermic needle 140 may be affixed to syringe head 70. Fluid 25 may be loaded into the barrel 50 of the ultrasonic syringe 10 and sonicated by the radiation surface of the transducer tip 30 as the fluid is injected from the barrel 50 through the hypodermic needle 140 into a patient. Similarly, fluid may be sonicated by the radiation surface 40 of the transducer tip 30 while the fluid 25 is withdrawn through the hypodermic needle 140 into the barrel 50 of the ultrasonic syringe 10 from the patient.

The ultrasound generator 15 may produce an electrical signal having various frequencies. The electrical signal may be then supplied to the ultrasound transducer 20 to drive the ultrasound transducer 20. A power source such as a battery or mains electric may be connected to the ultrasound generator 15 to provide electrical power to the ultrasound generator 15 for generation of the electrical signal. The ultrasound generator 15 may be configured to produce an electrical signal having a constant signal frequency or may be configured to produce an electrical signal having a variable signal frequency controllable by, for example, the practitioner.

In some embodiments, the signal frequency may be controlled automatically by the ultrasound generator 15. Such embodiments of the ultrasound generator may include feedback from the ultrasound transducer 20 and/or the transducer tip 30 so that the ultrasound generator 10 may detect resonance of the transducer tip 30. The ultrasound generator 10 may then adjust the frequency of the electrical signal in order to resonate the transducer tip 30.

The ultrasound transducer 20 converts the electrical signal supplied by the ultrasound generator 15 into a mechanical oscillation. The transducer tip 30 may be mechanically connected to the ultrasound transducer 20 so that the mechanical oscillation may be transmitted to the transducer tip 30 by the ultrasound transducer 20 to excite the transducer tip 30. The mechanical oscillation has an oscillation frequency that generally corresponds to the signal frequency supplied to the ultrasound transducer 20 by the ultrasound generator 15. Thus, the transducer tip 30 may be excited by the ultrasound transducer 20 at an oscillation frequency that generally corresponds to the signal frequency supplied to the ultrasound transducer 20 by the ultrasound generator 15.

The signal driving the ultrasound transducer may be a sinusoidal wave, square wave, triangular wave, trapezoidal wave, or any combination thereof.

The ultrasound transducer 20 may use piezoelectric crystals which have the property of changing size in response to changes in voltage to excite the transducer tip 30. Alternatively, the ultrasound transducer 20 may employ magnetostrictive materials or may be configured in other ways that would be recognized by those skilled in the art upon review of the present disclosure.

The transducer tip 30 may be excited at an oscillation frequency by the ultrasound transducer 20, which may induce a corresponding tip vibration in the transducer tip 30. The tip frequency, meaning the frequency at which the transducer tip 30 vibrates, may generally approximate the oscillation frequency and harmonics of the oscillation frequency of the ultrasound transducer 20. Accordingly, the tip frequency of the transducer tip 30 may be controlled by adjusting the signal frequency produced by the ultrasound generator 15 and, hence, the oscillation frequency of the ultrasound transducer 20.

The horn utilized may be capable of vibrating in resonance at a frequency of approximately 16 kHz or greater. The ultrasonic vibrations traveling down the horn may have an amplitude of approximately 1 micron or greater. It is preferred that the horn utilized be capable of vibrating in resonance at a frequency between approximately 20 kHz and approximately 200 kHz.

The transducer tip 30 may be configured to resonate generally at the signal frequency of range of signal frequencies produced by the ultrasound generator 15 so that the transducer tip 30 resonates when exited by the ultrasound transducer 20. The transducer tip 30 may be configured with a radiation surface 40 which may be generally a distal portion of the transducer tip 30. Ultrasonic waves 90 generated by excitation of the transducer tip 30 may then emanate from the radiation surface 40.

The barrel 50 of the ultrasonic syringe 10 defines an interior barrel surface 52 and an exterior barrel surface 54, and the interior barrel surface 52 defines a passage 56. Portions of the transducer tip 30 including the radiation surface 40 may extend into the passage 56 and may be sealably and slideably received within said passage 56 so that the portions of the transducer tip 30 including the radiation surface 40 in combination with the interior barrel surface 52 define a cavity 58 capable of containing the fluid 25 with the passage 56. A seal 80 or combination of seals 80 may be provided in some embodiments such that the transducer tip 30 may be sealably received within the passage 56. The seal 80 may be constructed of a resilient elastomer to reduce the transmission of vibrations from the transducer tip to the barrel and the hypodermic needle 140. A portion of the cavity 58 may be defined by the radiation surface 40 so that ultrasonic waves emitted from the radiation surface would be directed into the fluid 25 contained within the cavity 58 to sonicate the fluid 25.

The barrel 50 may also be configured with a syringe head, which may be a point of attachment for a hypodermic needle 140. The syringe head 70 may be formed in portions of the exterior barrel surface 54. Various features may be included in the syringe head 70 for the attachment of a hypodermic needle 140 such as seals and threading. In some embodiments, a portion of the interior barrel surface 52 may be configured as an orifice 60 to form a path of fluid communication between the cavity 58 and the syringe head 70 so that fluid 25 may pass between the cavity 58 and the hypodermic needle 140 attached at the syringe head through the orifice 60 for delivery to or withdrawal from the patient.

The hypodermic needle 140 may be a hollow needle that defines a needle lumen 146 from a proximal needle end 144 to a distal needle end 142 through which the fluid 25 may pass for delivery to or from a patient. The hypodermic needle 140 may be made of stainless steel or other suitable materials. The proximal needle end 144 may be configured for attachment to the ultrasonic syringe 10 at the syringe head 70. When attached to the ultrasonic syringe 10, the needle lumen 146 may be in fluid communication with the cavity 58 so that fluid 25 may pass between the cavity 58 and the distal needle end 142. The distal needle end 142 may be formed into a point, may include a sharpened edge, and otherwise configured to readily puncture skin and other bodily tissues. The hypodermic needle 140 may be of various sizes which may be selected by the practitioner depending upon the particular application.

In some embodiments, the volume of the cavity 58 may be adjusted by sliding the transducer tip 30 within the passage 56. By sliding the transducer within the passage 56, fluid 25 may be forced from the cavity 58 through the orifice 60 and through the hypodermic needle 140 and delivered to the patient. Similarly, by sliding the transducer tip 30 within the passage 56, fluid 25 may be withdrawn from the patient through the hypodermic needle 140 attached at the syringe head 70, through the orifice 60 and into the cavity 58. Such embodiments would be useful, for example, for the delivery of a single measured dose of fluid 25 to a patient. Accordingly, the barrel may include various marking indicative of the volume of the cavity 58 passed upon the position of the transducer tip 30 within the passage 56.

In other embodiments, the volume of the cavity 58 may remain relatively constant. In these embodiments, the barrel 50 may further include an attachment stub 130 configured, for example, to allow fluid communication between a reservoir and the ultrasonic syringe 10 so that the ultrasonic syringe could be used to deliver, for example, saline solution to the patient. The attachment stub 130 may be configured in various ways to enable connection of the ultrasonic syringe 10 to the reservoir of fluid 25 and may include various attachment mechanisms as would be understood by those skilled in the art upon review of this disclosure. A tube, for example, may be attached to the reservoir and to the attachment stub 130. The tube may be attached to a reservoir to form a path of fluid communication between the reservoir and the cavity 58 which passes through the tube and through the attachment stub 130. The attachment feature may include a valve 110 configured to control the flux of fluid 25 through the attachment stub 130. Such embodiments may be useful for a more continuous delivery of fluid 25 to or from the patient.

The ultrasound energy may be used to activate the therapeutic agent either directly or indirectly through oxygenation, the production of free radicals and/or ozone. The potential for ultrasound to produce cavitation and micro-streaming can be utilized for some embodiments.

Turning now to the Figures, aspects of the present inventions including the ultrasonic syringe 10 may be depicted in FIG. 1. The ultrasonic syringe 10 comprises an ultrasound generator 15 connected to a movable ultrasound transducer 20, a transducer tip 30 located at the distal end of the ultrasound transducer 20, a radiation surface 40 at the distal end of the transducer tip 30, a barrel 50, an orifice 60 located at the front end of barrel 50 and a syringe head 70. The ultrasound transducer 20 may be integral with the transducer tip 30 as to form a single part. Alternatively, the ultrasound transducer 20 may be a separate piece attached to the transducer tip 30 by mechanical or other means. The means of attaching the ultrasound transducer 20 to the transducer tip 30 may be such as to allow the ultrasound transducer 20 to be removed and replaced by the practitioner. Transducer tip 30 may be formed in a variety of shapes, such as, but not limited to, flat, round, and/or any combination thereof. Ultrasound transducer 20 may be integral with the barrel 50 so as to form a single part. Alternatively, the ultrasound transducer 20 may be a separate piece attached to barrel 50 by mechanical or other means. It may be preferable to have ultrasound transducer 20 detachable from barrel 50. A detachable and/or removable ultrasound transducer 20 from the barrel 50 enables the practitioner to change barrel 50, clean and/or sanitize ultrasound transducer 20 and/or barrel 50. Furthermore, the ability to change barrel 50 reduces the spread of diseases. Ultrasound transducer 20 may be connected to ultrasound generator 15. Alternatively, ultrasound transducer 20 may be battery operated whereby the battery (not shown) is inserted and/or imbedded into the ultrasound transducer 20.

FIG. 1 depicts a side view of an embodiment of the ultrasonic syringe 10 apparatus of the present invention where ultrasound transducer 20 may be slideably disposed inside the barrel 50. As illustrated in this embodiment, a portion of the barrel may be configured to define an aperture 100 configured so that the transducer tip 30 may slideably pass through the aperture 100.

As the ultrasound transducer 20 may be activated, ultrasonic waves 90 traveling at a preselected frequency, amplitude, intensity and/or signal form may be sent through the ultrasound transducer 20 to the transducer tip 30 and emitted from the radiation surface 40. Radiation surface 40 of the present invention may be formed in a variety of shapes, such as, but not limited to, flat, conical, rounded and/or any combination thereof. A flat surface may be preferred for embodiments that do not prefer focusing of the ultrasound waves. The proximal end of barrel 50 may be the area in which the ultrasound transducer 20 may be either attached permanently and/or detachable from the barrel 50. The syringe head 70 may be located at the distal end of barrel 50. Alternatively, barrel 50 may have an opening or orifice 60 located at the back end that receives a detachable and/or removable ultrasound transducer 20.

Figure 2:
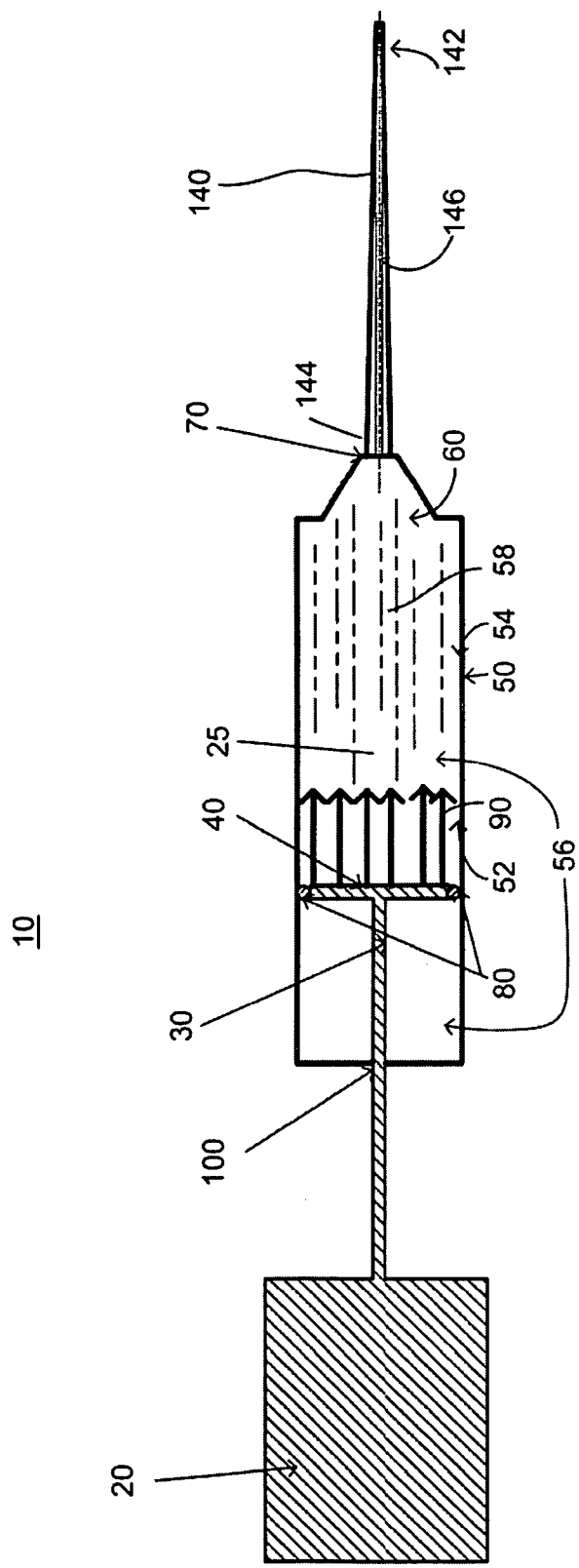
FIG. 2 illustrates a schematic view of aspects of an embodiment of an ultrasonic syringe according to the present inventions.

Referring to FIG. 2, a seal 80 prevents fluid 25 from exiting the cavity 58 by passing around portions of the transducer tip 30. Seal 80 also prevents air from entering into the cavity 58. Barrel 50 may be pre-filled with fluid 25 to be injected or the ultrasonic syringe 10 may be filled by mechanically and/or manually pulling back ultrasound transducer 20. Ultrasound transducer 20 imbedded and/or attached to barrel 50 may be activated with fluid 25 present within barrel 50. Ultrasound transducer 20 may be then depressed either mechanically by a motor (not pictured) and/or manually by pushing down ultrasound transducer 20. Ultrasonic energy at a pre-selected frequency may be sent through transducer tip 30 as ultrasound transducer 20 may be being depressed. Depressing ultrasound transducer 20 pushes the fluid 25 in the barrel 50 forward towards center orifice 60.

As shown in FIGS. 1 and 2, the ultrasound transducer 20 may be movable, and depresses forward towards the front end of the barrel 50 when pushed, mechanically and/or manually, and moves backwards towards the back end of barrel 50 when fluid 25 may be being withdrawn from the patient. When ultrasound transducer 20 may be pulled back towards the back end of the barrel 50, it creates a vacuum which enables fluid 25 to be withdrawn from the patient through center orifice 60 into the barrel 50. Ultrasound transducer 20 moves forwards and backwards within barrel 50. Radiation surface 40 emits ultrasonic waves 90 inducing vibrations and sonicating the fluid 25 within the barrel 50 prior and during delivery to patient. The adjustability of the cavity 58 portion of the barrel 50 allows for the optimization of standing waves to be generated in the cavity 58. This allows the enhancement of micro cavitation and micro-streaming as desired. Furthermore disinfection properties of the apparatus may be enhanced. Adjustability of the barrel also allows control of the ultrasonic interaction of the ultrasound transducer 20 with hypodermic needle 140. This permits focusing of ultrasound at or through the needle if desired.

Ultrasound transducer 20 may be fully depressed with radiation surface 40 pushing out the sonicated fluid 25 through center orifice 60 into the body via hypodermic needle 140. Hypodermic needle 140 may be affixed to syringe head 70 by mechanical mean or other means. Hypodermic needle 140 may be variable in size depending oil the designated use, such as, but not limited to use on large farm animals, such as cows, and horses.

Figure 3:
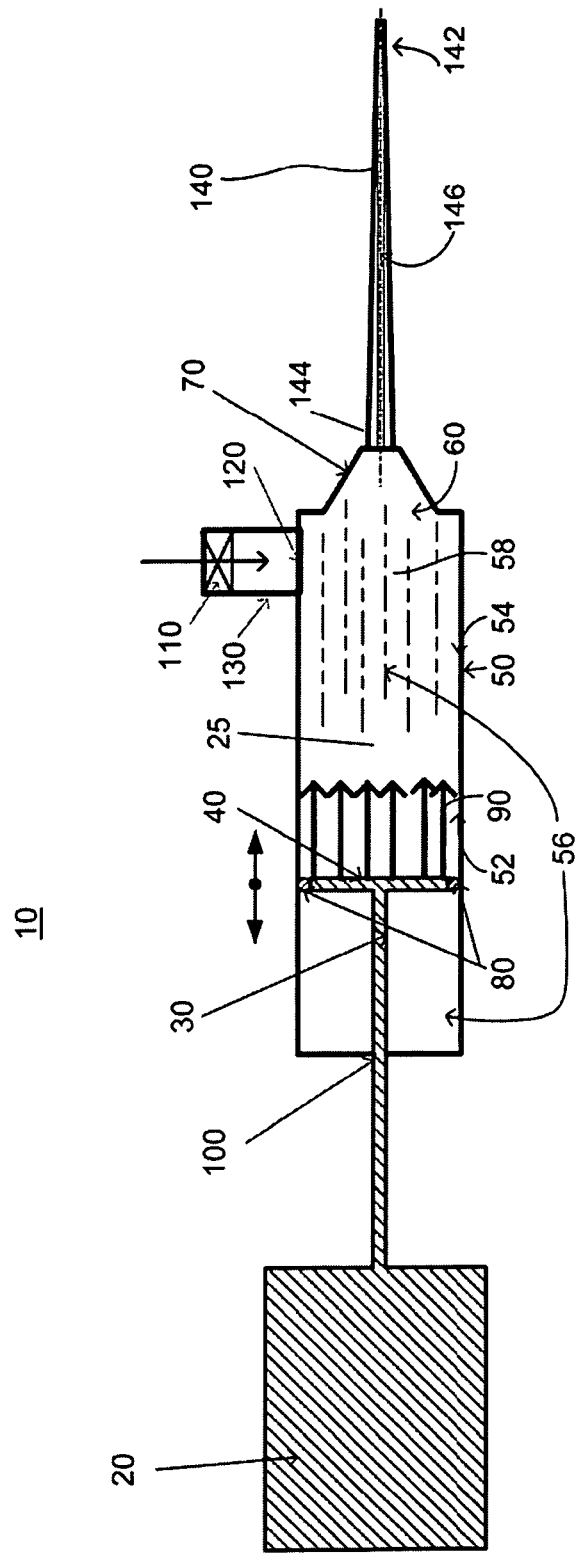
FIG. 3 illustrates a side view of aspects of an exemplary embodiment of an ultrasonic syringe according to the present invention including an attachment stub.

FIG. 3 depicts a cross-sectional view of an alternative embodiment of the ultrasonic syringe 10 apparatus of the present invention comprising a port 120 within the side wall of barrel 50, a attachment stub 130, and a valve 110 at the distal end of attachment stub 130. Attachment stub 130 originates from port 120 and terminates at valve 110. The valve 110 depicted may be manually controlled, although mechanically and/or automatically controlled valves including check valves may also be used with the present invention. Fluid 25 may be introduced through valve 110 into attachment stub 130. Fluid 25 may flow through attachment stub 130, entering through port 120 into barrel 50. Valve 110 prevents fluid 25 entering into barrel 50 through port 120 on the side wall of barrel 50 from flowing back out of port 120 on side wall of barrel 50 into attachment stub 130. Preferably, this alternative embodiment may be used for delivery of fluid 25 to the patient. Activating ultrasound transducer 20 creates ultrasound vibrations within the fluid 25 in barrel 50. Ultrasonic waves 90 coming in contact with fluid 25 within the barrel 50 sonicate the fluid 25 prior and during delivery to patients. Sonicated fluid 25 may be pushed through orifice 60 by a combination of the ultrasonic waves 90 and the depressing of ultrasound transducer 20.

Although specific embodiments have been illustrated and described herein, it will be appreciated by those of ordinary skill in the art that any arrangement that is calculated to achieve the same purpose may be substituted for the specific embodiments. It is to be understood that the above description is intended to be illustrative and not restrictive. The disclosed steps of the methods are not intended to be restricted to the order listed. Combinations of the above embodiments and; other embodiments will be apparent to those having skill in the art upon review of the present disclosure. The scope of the present invention should be determined with reference to the appended claims, along with the full scope of equivalents to which such claims are entitled.

I claim:

1. A method for delivery or withdrawal of a fluid comprising the steps of:
   filling a barrel of an ultrasonic syringe with a fluid;
   activating an ultrasound transducer at a frequency of approximately 20 kHz or greater;
   transmitting ultrasound energy through a transducer tip;
   vibrating a radiation surface of a distal end of the transducer tip;
   sonicating the fluid within a cavity of the barrel; and
   utilizing the ultrasound energy to assist ejecting the sonicated fluid from the cavity.

2. The method of claim 1 characterized by the fluid being a therapeutic agent.

3. The method of claim 1 wherein the step of sonicating the fluid provides activation of the fluid.

4. The method of claim 3 wherein the step of sonicating the fluid also produces ozone.

5. The method of claim 3 wherein the step of sonicating the fluid also produces free radicals.

6. The method of claim 3 wherein the step of sonicating the fluid also produces cavitation.

7. The method of claim 3 wherein the step of sonicating the fluid also produces standing waves within the cavity.

8. The method of claim 1 characterized by the fluid including an antibiotic.

9. The method of claim 1 characterized by the fluid including an anesthetic.

10. The method of claim 1 also including the step of focusing the ultrasound energy.

11. The method of claim 1 also including the step of focusing the ultrasound energy through a hypodermic needle.

12. The method of claim 11 having the additional step of removing the hypodermic needle from the barrel.

13. The method of claim 1 having the additional step of moving the radiation surface within the barrel.

14. The method of claim 1 wherein the step of sonicating the fluid also produces anesthetic effects.

15. The method of claim 1 wherein the step of sonicating the fluid within the cavity also activates a therapeutic agent.

16. The method of claim 1 wherein the radiation surface emits ultrasound waves at a frequency between 20 kHz and 20 mHz.

17. The method of claim 1 wherein the radiation surface emits ultrasound waves at a wavelength within a range of 1 micron to 300 microns.

18. A method for delivery or withdrawal of a fluid comprising the steps of:
    supplying a fluid to an ultrasonic syringe through an attachment stub in fluid communication to a barrel;
    filling the barrel with the fluid;
    activating an ultrasound transducer at a frequency of approximately 20 kHz or greater;
    transmitting ultrasound energy through a transducer tip;
    vibrating a radiation surface of a distal end of the transducer tip;
    sonicating the fluid within a cavity of the barrel; and
    utilizing the ultrasound energy to assist ejecting the sonicated fluid from the cavity.

19. The method of claim 18 also including the step of controlling the fluid with a valve portion of the attachment stub.

* * * * *